United States Patent [19]

Nakayama et al.

[11] Patent Number: 5,133,968

[45] Date of Patent: Jul. 28, 1992

[54] MODIFIED PROTEASE, METHOD OF PRODUCING THE SAME AND COSMETIC PRODUCTS CONTAINING THE MODIFIED PROTEASE

[75] Inventors: Hiroshi Nakayama, Hirakata; Shinichi Fukunaga; Yasumitsu Fujino, both of Osaka; Kenji Mori, Odawara, all of Japan

[73] Assignee: Kanebo, Ltd., Tokyo, Japan

[21] Appl. No.: 570,077

[22] Filed: Aug. 20, 1990

[51] Int. Cl.$^5$ .............. A61K 7/40; A61K 7/48; A61K 37/54; A61K 37/547

[52] U.S. Cl. .............. 424/401; 424/94.1; 424/94.63; 424/94.64

[58] Field of Search ............. 424/94.1, 94.63, 94.64, 424/401

[56] References Cited

U.S. PATENT DOCUMENTS 3,639,213  2/1972  Ginger et al. ............... 424/94.64
4,746,675  5/1988  Makino et al. ............... 514/946

FOREIGN PATENT DOCUMENTS 0023244    11/1967  Japan ................... 424/94.64
WO79/00609  8/1979  PCT Int'l Appl. .
2150833     7/1985  United Kingdom .

OTHER PUBLICATIONS

Prikl. Biokhim Mikrobiol (1979) 15(1): 82-87.

Primary Examiner—Thurman K. Page
Assistant Examiner—C. Azpuru
Attorney, Agent, or Firm—Armstrong & Kubovcik

[57] ABSTRACT

The invention provides a modified protease such that a protease is coupled to a polysaccharide via a triazine ring. This modified protease is considerably stable, safe and active as compared with the conventional modified proteases and immobilized proteases. Therefore, cosmetic products containing this modified protease are less liable to undergo aging, easier to use and improved in effect on the skin.

4 Claims, No Drawings

5,133,968

MODIFIED PROTEASE, METHOD OF PRODUCING THE SAME AND COSMETIC PRODUCTS CONTAINING THE MODIFIED PROTEASE

TECHNICAL FIELD

The present invention relates to a polysaccharide-modified protease, a method of producing the same, and a cosmetic composition containing said modified protease.

BACKGROUND OF THE INVENTION

Proteases of animal, vegetable or microbial origin are commonly used with advantage in a variety of applications such as detergents, pharmaceutical composition, e.g. digestants, antiinflammatory drugs, etc., cosmetics, meat tenderizing agents, silk scouring agents, beer production and so on.

However, it has been pointed out that being proteins heterogenous to man, these protease in detergents, cosmetic and pharmaceutical products, etc. present antigenicity and dermal hypersensitivity problems and at times elicit intense irritable responses depending on individuals. A further problem with these enzymes is that they are relatively labile.

Particularly in media rich in water or in aqueous solutions, proteases are not only denatured but also undergo autolysis. It is also known that storage at ambient temperature results in rapid inactivation. Therefore, it has heretofore been difficult to supply the consumer with stable protease-containing products.

In order to solve the antigenicity and other safety problems with this type of enzyme, namely for suppressing the antigenicity and prolonging the blood half-life of the enzyme in systemic regimens for the treatment of diseases, it has been proposed to modify uricase or asparaginase with polyethylene glycol (Japanese Patent Publication No. 61-42558) or modify streptokinase with polyethylene glycol (Japanese Kokai Patent Publication No. 57-118789). As an approach to the stability problem of proteases, it has been shown with chymotrypsin and certain other enzymes that a chemical modification contributory to intramolecular bridging is effective (Biochimica et Biophysica Acta 522, 277-283, 1987 and 485, 1-12, 1977). Furthermore, it has been demonstrated that the binding of a water-soluble polymer such as a polysaccharide, polyethylene glycol, a protein or the like to a manganese superoxide dismutase results in suppression of the antigenicity and improvement of the thermal stability of the enzyme (Japanese Kokai Patent Publication No. 58-16685).

However, there is not known an implementation technology which would contribute to reduction of the antigenicity and skin sensitization potentials and, at the same time, to the stability of the enzyme. Since dermal hypersensitivity, inter alia, is a very delicate reaction, the inhibition of this reaction is technically a very difficult proposition. Moreover, since the substrate of proteases are generally high molecular weight substances, their enzymatic activity and their thermal stability are seriously sacrificed by such modification depending on the degree of modification. Therefore, any modification of the enzymes is also very difficult.

Therefore, the inventors of the present invention explored into this realm of technology with a view to improving the stability of proteases without sacrificing their activity in order that those enzymes may be better exploited in a broad spectrum of uses such as detergents, cosmetics, drugs and so forth. The above exploration and subsequent research resulted in accomplishment of the present invention.

The present invention is therefore directed to a modified protease with reduced skin sensitization and antigenic potentials, improved stability and high activity, a method of producing such modified protease, and a cosmetic composition containing the modified protease.

SUMMARY OF THE INVENTION

To accomplish the above-mentioned objects, the present invention provides (1) a modified protease such that a protease is linked to a polysaccharide via a triazine ring, (2) a method of producing a modified protease which comprises reacting a polysaccharide with cyanuric trichloride to synthesize a triazine ring-bound polysaccharide and reacting this triazine ring-bound polysaccharide with a protease, and (3) a cosmetic composition containing a modified protease in which a protease is linked to a polysaccharide via a triazine ring.

The present invention is described below in detail.

DETAILED DESCRIPTION OF THE INVENTION

The proteases which can be employed in the practice of the invention include proteases of animal origin, such as trypsin, chymotrypsin, etc. and those of microbial origin, although proteases derived from microorganisms are superior to those derived from animals in the aspect of stability. Therefore, particularly beneficial results can be obtained with the use of a microbial protease, especially a protease derived from Bacillus organisms.

The polysaccharides which can be used for the purposes of the invention include various naturally-occurring polysaccharides, such as agarose, guar gum, inulin, starch, dextran, pullulan, xanthan gum, carrageenin, pectin, alginic acid, etc. and derivatives thereof, hydroxypropylcellulose, methylcellulose, ethylcellulose, carboxymethylcellulose and so on. Particularly, dextran and pullulan are advantageous in that, even if those of fairly high molecular weight are employed, they provide solution viscosities low enough to facilitate the reaction and that the resulting modified protease is more uniform in performance and stable.

Regarding the molecular weight of such polysaccharide, the suppressing effect of the invention on antigenicity and dermal hypersensitivity will not be sufficient if the molecular weight is too low. Therefore, it is desirable to employ a polysaccharide with an average molecular weight not less than 10,000 and preferably not less than 40,000.

The degree of suppression of antigenicity and dermal hypersensitivity response and the degree of stabilization which can be achieved by modification with respect to the unmodified protease are not only dependent on the kind and molecular weight of the polysaccharide used but also vary with the degree of modification. The modification rate for surface amino groups in the modified protease of the present invention, as determined by the TNBS method described below, is preferably not less than 30% and more desirably not less than 50%.

TNBS METHOD

According to the method of Haynes (Haynes, R. et al., Biochemistry 6, 541, 1967), the amount of unreacted amino groups on the surface of the modified protease is measured as the amount of reaction of trinitrobenzenesulfonic acid (TNBS) and the modification rate for surface amino groups is calculated from the ratio of said amount to the amount of surface amino groups of the unmodified protease.

The method for production of a modified protease according to the present invention is described below.

The modified protease of the invention can be produced by reacting said polysaccharide with cyanuric trichloride to give a triazine ring-bound polysasccharide and reacting this reaction product further with a protease. A modified protease of still more stable quality can be obtained by subjecting the above reaction product to an after-treatment which comprises addition of lysine, glycine, aminoethanol or the like for blocking excess active groups of the polysaccharide. The thus-obtained modified protease can be purified by per se known techniques such as ultrafiltration, gel filtration, liquid chromatography and so on. If desired, the product modified protease may be processed into a finely divided preparation.

In the production method described above, a more stable modified protease can be obtained with improved reproducibility by ensuring, in the stage of reacting the triazine ring-bound polysaccharide with the protease, that the reactive chlorine content of said triazine ring-bound polysaccharide is 0.4 to 1.2 mmol (milligram atoms)/gram and that the molar ratio of the chlorine to the reactive amino groups of the protease is not less than 2. In order to assure such a reactive chlorine content of triazine ring-bound polysaccharide, it is advantageous to employ, as the solvent for cyanuric trichloride solution in the reaction thereof with the polysaccharide, a non-aqueous solvent which is miscible with water and inert to cyanuric trichloride. It is also recommended that the reaction be conducted while the reaction system comprising a solution of cyanuric trichloride and a solution of said polysaccharide is controlled at pH 7.5 to 9.5, particularly at pH 8 to 9. As examples of said non-aqueous solvent for use in the preparation of said solution of cyanuric trichloride, there may be mentioned acetone, tetrahydrofuran, dioxane, dimethyl sulfoxide and so on. In consideration of the ease of use and subsequent removal, acetone is the most advantageous of all. There may be cases in which the cyanuric trichloride solution is preferably diluted with water but since cyanuric trichloride is decomposed with time in the presence of water, it is then necessary to add such cyanuric trichloride solution to the aqueous polysaccharide solution without delay after preparation.

By the method described above, the necessary active groups can be introduced into the polysaccharide with good reproducibility, the reaction efficiency be improved, and the amount of cyanuric trichloride be decreased. The amount of introduction of active groups can be controlled at a desired level by adjusting the ratio of the polysaccharide to cyanuric trichloride and, for the purposes of the present invention, the ratio of polysaccharide to cyanuric trichloride to be reacted is preferably in the range of 1:0.5 to 1:0.1 by weight. The reaction temperature is preferably in the neighborhood of room temperature (15° to 25° C.). In consideration of the fact that the decomposition of the active groups introduced into the polysaccharide are time-dependent, the reaction time is preferably not over 30 minutes. The reaction can be stopped by acidifying the reaction system to about pH 3.

In conducting the coupling reaction between the triazine ring-bound polysaccharide and protease, it is good practice to use at least 3 times as much of the triazine ring-bound polysaccharide based on the weight of the protease and ensure that the molar ratio of the reactive chlorine of the triazine ring-bound polysaccharide to the reactive amino groups of the protease is at least 2 times. It is still more desirable that the molar ratio of reactive chlorine to reactive amino groups be not less than 5 times. The larger this ratio, the higher is the enzyme modification rate and particularly when the molar ratio is 5 times or more, a very stable modified protease is obtained. While a fairly stable modified protease is still obtained even if the above-mentioned weight ratio of activated polysaccharide to protease is not satisfied, the suppressive effect on antigenicity and dermal hypersensitivity response is not sufficient.

Furthermore, the stability of the modified protease tends to increase with an increasing modification rate but the yield of enzyme activity is then rather reduced in some degree. Therefore, when the product form is one contributory to enhanced stability of protease, a somewhat lower modification rate can be selected. Depending on the purity of protease used, other proteinous components and low molecular amino group-containing substances may be present and these amino groups react with the reactive chlorine of the activated polysaccharide to alter the modification rate of the protease. Therefore, the term 'reactive amino groups of protease' is used herein to mean globally the surface amino groups of the protease plus the amino groups of said contaminant substances.

A modified protease of stable quality, even in a powdery state, can be obtained when the amount of atomic halogen bound to the triazine ring of the product modified protease is decreased to 500 ppm in the after-treatment which is carried out following the coupling reaction of the protease and polysasccharide. In this after-treatment, the modified protease obtained by the coupling reaction is treated preferably in an aqueous solution of an amino-containing low molecular compound. While the type of amino-containing low molecular compound is not critical, there may be employed amino acids such as glycine, alanine, lysine, serine, glutamic acid, etc., monoethanolamine and other compounds which are not conducive to hypersensitivity reactions and do not adversely affect the structure of the modified protease. The number of halogen atoms bound to the triazine ring which remain in the modified protease decreases with the duration of treatment and the rate of decrease tends to increase as the temperature and/or pH is increased. Therefore, in order to insure a high treatment efficiency while avoiding the denaturation and inactivation of the protease, the treatment system is maintained at pH 6.5 to 9.5. The treating temperature is preferably 50° to 75° C. and, for still better results, 55° to 70° C. If the temperature is too low, it takes a long time to reduce the amount of bound atomic halogen to not more than 500 ppm. Conversely when the treating temperature is too high, the inactivation of protease progresses in paralle with the effect of after-treatment so that the activity of the modified protease is sacrificed. The above-mentioned temperature range is also desirable in view of the ease of control. The treating time is dependent on treating temperature and pH. As already mentioned, the modified protease thus after-treated is stable in quality even in finely powdery state, thus permitting the production of a powdery preparation of modified protease. For the production of such finely powdery modified protease, such techniques as vacuum evaporation, freeze-drying, precipitation from a poor solvent such as ethanol, etc. can be employed.

Using the modified protease according to the invention, a variety of cosmetic products can be manufactured. In such cosmetic products, it is advantageous to incorporate 0.0001 to 5 weight parts (hereinafter referred to briefly as parts) of said modified protease based on 100 parts of the cosmetic material. If the proportion of modified protease is less than 0.0001 part, the protease does not function fully as expected in the cosmetic material, while the use of modified protease in excess of 5 parts does not insure any further improvement in the expected result.

The cosmetic material mentioned above includes, among others, various kinds of skin cream, skin milk, cleansing cream, cleansing lotion, cleasing milk, cold cream, cream soap, makeup base, skin lotion, milky lotion, pack, calamine lotion, T zone essence, hand cream, essence powder, whitening powder, powder soap, cake soap, transparent soap, lip cream, lipstick, nourishing essence, creamy foundation, face powder, powder eye-shadow, powder foundation, nail remover, hair tonic, hair liquid, hair cream, hair treatment, scalp treatment, shampoo, rinse, hair spray, sun oil, sun screen, shaving foam, shaving cream, baby oil and so forth.

The following examples and comparative examples are further illustrative of the invention.

EXAMPLE 1

In 50 ml of water was dissolved 2.5 g of dextran (average molecular weight $4 \times 10^4$). To this solution was added a solution of 1,3,5-trichlorotriazine (cyanuric trichloride) (1 g) in a mixed solvent of water-acetone (0.5:2.5, v/v) (35 ml) dropwise at room temperature over a period of 8 minutes while the system was maintained at pH 7.5 to 9.5. The adjustment of pH was carried out with 1 N-NaOH. After completion of dropwise addition, the reaction system was adjusted to pH 3 with 0.1 N-HCl and poured in 500 ml of acetone. The resulting crystals were collected by filtration and washed with acetone to give an activated dextran.

Then, 20 mg of a protease derived from Bacillus licheniformis (Esperase, manufactured by Novo) was dissolved in 10 ml of 0.1M borate buffer (pH 9.2) followed by addition of 0.2 g of the above activated dextran. The mixture was reacted at 4° C. for 24 hours. This reaction mixture was treated with 40 mg of glycine at 62° C. for 24 hours, at the end of which time the solution was subjected to ultrafiltration, purified, concentrated and lyophilized. The resulting lyophilized powder was sterilized by heating at 105° C. for 2 hours.

The modification rate for surface amino groups (as determined by the method described hereinbefore) of this modified protease was 75% and the precentage residual enzyme activity was 65%.

EXAMPLE 2

The procedure of Example 1 was repeated except that pullulan (average molecular weight: 50,000) was used in lieu of dextran and bioprase (manufactured by Nagase Biochemical) was used as the protease to give a modified protease.

The modification rate for surface amino groups of the above modified protease was 79% and the percentage residual activity was 62%.

EXAMPLE 3

The procedure of Example 1 was repeated except that methylcellulose was used in lieu of dextran to give a modified protease.

The modification rate for surface amino groups of the above modified protease was 68% and the percentage residual activity was 67%.

EXAMPLE 4

The procedure of Example 1 was repeated except that inulin (average molecular weight: 50,000) was used in lieu of dextran and bioprase was used as the protease to give a modified protease.

The modification rate for surface amino groups of the modified protease was 71% and the percentage residual activity was 45%.

COMPARATIVE EXAMPLE 1

In 30 ml of anhydrous acetonitrile were dissolved 5.0 g of monomethoxy polyethylene glycol (average molecular weight: 5,000) and 0.6 g of p-nitrophenyl chloroformate followed by addition of 0.3 g of triethylamine. The mixture was stirred at an ambient temperature of 25° C. for 24 hours, at the end of which time 200 ml of diethyl ether was added. The mixture was allowed to stand at 4° C. for 24 hours to allow crystallization to proceed. The resulting crystals were harvested by filtration, recrystallized from a mixed solvent of diethyl ether-acetonitrile, washed well with diethyl ether, and dried under reduced pressure to give 4.5 g of an activated polyethylene glycol as white crystals.

Then, 50 mg of the same protease as used in Example 1 was dissolved in 20 ml of 75 mM potassium phosphate buffer (pH 7.8) followed by addition of 100 mg of the above activated polyethylene glycol. The mixture was stirred at 4° C. for 24 hours. This reaction mixture was treated with 100 mg of glycine for 5 hours and, then, purified by ultrafiltration, concentrated and lyophilized.

The percentage residual activity of the modified protease thus obtained was 28%.

COMPARATIVE EXAMPLE 2

In 25 ml of 0.1M phosphate buffer (pH 6.5) was dissolved 50 mg of the same protease as used in Example 1 followed by addition of 1.5 ml of 1.4% aqueous glutaraldehyde solution dropwise at room temperature with stirring over a period of 25 minutes. The mixture was further stirred for 2 hours, at the end of which time 10 mg of glycine was added. After 5 hours of this treatment, 10 mg of sodium borohydride was added for reduction reaction and the reaction mixture was purified by ultrafiltration, concentrated and lyophilized.

The residual activity of this modified protease was 48%.

COMPARATIVE EXAMPLE 3

In 20 ml of water was dissolved 200 mg of carboxymethyl cellulose and the solution was adjusted to pH 4.75 with 1N-HCL. To this solution were added 380 mg of 1-ethyl-3-(3-dimethylaminopropyl) carbodiimide hydrochloride and 20 mg of the same protease as used in Example 1 and the mixture was stirred at 4° C. for 2 hours. To this reaction mixture were added 120 µl of acetic acid and 120 µl of monoethanolamine and the mixture was stirred for 20 minutes. Finally the solution was purified by ultrafiltration, concentrated and lyophilized.

The residual acitivity of this modified protease was 52%.

COMPARATIVE EXAMPLE 4

In 100 ml of water was dissolved 0.5 g of the same dextran as used in Example 1 followed by addition of 0.32 g of sodium periodate. The mixture was reacted at 50° C. for 5 hours. The reaction was then stopped by addition of 50 ml of ethylene glycol and the unreacted material was removed by ultrafiltration. The filtrate was washed with 75 mmol phosphate buffer (pH 7.8) and concentrated to 10 ml. To this concentrate was added 50 mg of the same protease as used in Example 1 and the reaction was conducted at 4° C. for 24 hours. The reaction mixture was subjected to chemical reduction with NaBH$_4$ and the reduction product was purified by ultrafiltration, concentrated and lyophilized.

The percentage residual activity of this modified protease was 45%.

Table 1 shows the results of assessment of the thermal stability, skin sensitization potential and antigenicity of products according to Examples 1 to 4 and Comparative Examples 1 to 4. The assessment of thermal stability, skin sensitization potential and antigenicity of each product was carried out by the following methods.

Assessment of Thermal Stability

The test modified protease was dissolved in 50 mmol phosphate buffer (pH 6.8) to a concentration of 0.5 mg protein/ml. This test solution was incubated at 60° C. for 6 hours and the enzyme activity in the test solution was assayed.

Assessment of Skin Sensitization Potential

A dermal hypersensitivity test was performed by the maximization method (Bertil, M and Albert, M. K.; J. Invest. Derm. 52 (3), 268, 1969). The induction and challenge concentration was 0.05 weight % as protein for both intact protease and modified protease. The skin sensitization potential was expressed as the mean score calculated by the following equation.

$$\text{Mean score} = \frac{\Sigma \text{ intensity of reaction (0-5)}}{\text{Number of test animals}}$$

To 0.4 ml of a modified protease solution of a predetermined concentration (0.3 mg protein/ml) was added 0.4 ml of an antiserum separately provided and the mixture was incubated at 30° C. for 2 hours. The resulting precipitate was recovered by centrifugation, washed 3 times with 1 ml portions of 75 mmol phosphate buffer (pH 7.8) and dissolved in 3 ml of 0.1 N-NaOH. Using this solution, the absorbance at 285 nm was measured. Based on the absorbance value, the antigenicity of the sample was estimated according to the following criteria.

| Absorbance | Antigenicity |
| --- | --- |
| <0.1 | − |
| ≧0.1~<0.3 | ± |
| ≧0.3~<1.0 | + |

TABLE 1

|  |  | Residual activity (%) | Thermal stability (%) *1 | Skin sensitization potential *2 | Antigenicity |
| --- | --- | --- | --- | --- | --- |
| Unmodified |  | — | 12 | 4.9 | + |
| Examples | 1 | 65 | 98 | 0 | − |
|  | 2 | 62 | 82 | 0.1 | − |
|  | 3 | 67 | 80 | 0.3 | − |
|  | 4 | 45 | 85 | 0.1 | − |
| Comparative | 1 | 28 | 32 | 2.5 | + |
| Example | 2 | 48 | 38 | 4.6 | + |
|  | 3 | 52 | 40 | 2.4 | + |
|  | 4 | 45 | 70 | 2.1 | + |

*1: The modified protease was heat-treated and the % residual activity was determined.
*2: Mean score It is apparent from the above results that compared with the products according to Comparative Examples, all the modified proteases according to Examples of the invention, in which a polysaccharide is bound to a protease via a triazine ring, have been remarkably improved in thermal stability and suppressed in antigenicity and skin sensitization potential. Moreover, the products according to Examples feature a smaller loss of activity due to modification and exhibit higher activity.

EXAMPLES 5 to 10

Modified proteases were produced by the procedure of Example 1 except that the kind of dextran was varied as indicated in Table 2 and the activated dextran-protease ratio (by weight) was varied as also shown in Table 2. Furthermore, in the synthesis of the activated dextran, a solution of 1 g of cyanuric trichloride in 30 ml of acetone was used. The reactive chlorine content of the activated dextran was 1.0 mmol/g and the reactive amino groups content of the protease was 0.9 mmol/g. The modification rate for surface amino groups, residual activity, thermal stability and skin sensitization potential of the modified proteases obtained above were determined by the procedures described hereinbefore. The results are also set forth in Table 2.

The reactive chlorine content was determined by the following procedure.

Determination of Reactive Chlorine Content

In 4 ml of water was dissolved 100 mg of each sample followed by addition of 1 ml of 0.5 M-NaHCO$_3$. The mixture was heat-treated at 100° C. for 30 minutes, at the end of which time 0.5 ml of 7% aqueous chromic acid solution was added. After dilution with water, chlorine was titrated with 0.1N aqueous silver nitrate solution (The result was expressed as V$_1$ ml). As a control, a similar titration was carried out on samples without alkali treatment (The result was expressed as V$_0$ ml). From the difference (V$_1$−V$_0$), the equivalent amount of chlorine was calculated to estimate the reactive chlorine content.

TABLE 2

|  |  | Activated dextran/ protease | Average molecular weight of dextran ($\times 10^4$) | Modification rate for surface amino groups (%) | Residual activity (%) | Thermal stability (%) *1 | Skin sensitization potential *2 |
| --- | --- | --- | --- | --- | --- | --- | --- |
| Examples | 5 | 3/1 | 6~9 | 63 | 65 | 90 | 0.2 |
|  | 6 | 4/1 | 6~9 | 71 | 62 | 95 | 0.3 |
|  | 7 | 8/1 | 6~9 | 80 | 55 | 97 | 0.1 |
|  | 8 | 8/1 | 2 | 72 | 64 | 92 | 0.3 |
|  | 9 | 8/1 | 0.5 | 64 | 68 | 82 | 0.4 |
|  | 10 | 16/1 | 6~9 | 83 | 53 | 100 | 0 |

*1: The modified protease was heat-treated and the % residual activity was determined.
*2: Mean score It is apparent from the above results that the thermal stability of the modified protease can be remarkably improved and the skin sensitization potential thereof either reduced considerably or abolished by selecting the proper reaction ratio of activated dextran to protease.

The modified proteases prepared in Examples 1 to 4 and Comparative Examples 1 to 4 were respectively subjected to thermal stability testing in the presence of 10% of a surfactant. The results are set forth in Table 3.

TABLE 3

|  | Surfactant* |  | Residual activity (%) | | |
| --- | --- | --- | --- | --- | --- |
|  |  |  | not used | Triron X-100 | MES-7H |
| Type of Protease | Unmodified |  | 12 | 10 | 7 |
|  | Examples | 1 | 98 | 87 | 88 |
|  |  | 2 | 82 | 75 | 77 |
|  |  | 3 | 80 | 78 | 79 |
|  |  | 4 | 85 | 82 | 75 |
|  | Comparative | 1 | 26 | 18 | 15 |
|  | Examples | 2 | 23 | 14 | 11 |
|  |  | 3 | 27 | 21 | 19 |
|  |  | 4 | 31 | 24 | 20 |

*Triron X-100 (manufactured by Wako Pure Chemical)
MES-7H (manufactured by Nippon Shokubai Kagaku)

It is apparent from the above table that the modified protease (products of Examples) in which a polysaccharide is bound to a protease via a triazine ring invariably exhibits high thermal stability even in the presence of surfactants.

EXAMPLES 11 THROUGH 13

In 2.5 l of water was dissolved 125 g of same dextran as used in Example 1. To this solution was added a solution of 25 g of cyanuric trichloride in 625 ml of acetone dropwise at room temperature over a period of 8 minutes, with the pH of the system being controlled at pH 7 to 9 with 1N-NaOH. After completion of dropwise addition, the reaction mixture was adjusted to pH 3 with 0.1 N-HCl and poured in 20 l of acetone. The resulting crystals were harvested by filtration and washed with acetone to give 144 g of activated dextran.

In 90 ml of water was dissolved 9 g of the above activated dextran. To this solution was added a solution of 1 g of the same protease as used in Example 1 in 10 ml of water, followed by addition of 100 ml of 0.2M borate buffer (pH 9.2). The mixture was reacted at 25° C. for 18 hours.

Then, 1.2 g of glycine was dissolved in this aqueous modified protease solution and the solution was divided into 40 ml portions. These protions were heat-treated at 60° C. for the time periods indicated below in Table 4 and each treated solution was ultrafiltered 4 times to remove low molecular impurities, concentrated and lyophilized to give a brown powder.

The activity, chlorine content, modification rate for surface amino groups, and skin sensitization potential of the products of above Examples 11 to 13 were determined. Furthermore, the products were subjected to dry heat treatment at 60° C. for 7 days and then changes in water-solubility and activity of said treated products were evaluated. The results are set forth in Table 4. The chlorine content was determined by fluorescent X-ray analysis using a disk molded from 100 mg of the powder sample. The other parameters were determined by the procedures hereinbefore described.

TABLE 4

|  |  | Heat treating time (hr.) | Yield of activity *1 (%) | Modification rate for surface amino groups (%) | Chlorine content (ppm) | Skin sensitization potential | Powder after 7-day dry heat treatment at 60° C. | | |
| --- | --- | --- | --- | --- | --- | --- | --- | --- | --- |
|  |  |  |  |  |  |  | Water solubility | Residual activity (%) *2 | Thermal stability in aqueous medium (%) |
| Example | 11 | 12 | 51 | 89 | 950 | 0 | Slightly insolubilized | 81 | 97 |
|  | 12 | 24 | 51 | 89 | 280 | 0 | Readily soluble | 100 | 100 |
|  | 13 | 36 | 51 | 87 | 140 | 0 | Readily soluble | 100 | 100 |

*1: Calculated yield based on activity at synthesis
*2: % Residual activity with respect to activity prior to dry heat treatment It is apparent from the above results that while the modified protease having high chlorine content had a tendency of gelatinization (insolubilization in water) by a dry heat treatment, the samples having less than 500 ppm of the active chlorine content by thermal treatment had not gelatinization by the dry heat treatment and a little deterioration of activity. Deterioration in yield of activity and sensitization was not elicited and deterioration of thermal stability in the presence of water is not observed. Furthermore, from the values of the yield of activity of 24 and 36 hour-heat treated samples with less than 500 ppm chlorine content, it is found that deterioration of activity by the treatment is very small. Even if these samples are hot-air sterilized, the activity deterioration rate is less than 10% and change in physical properties was not seen at all.

EXAMPLE 14

The procedure of Examples 11 to 13 was repeated except that pullulan (average molecular weight: $5 \times 10^4$) was used in lieu of dextran to give a modified protease. Inactive treatment of active chlorine groups of its triazine ring was conducted at 63° C. for 24 hours after adding glycine, purified by ultrafiltration, then lyophilized to give 9.5 g of a product modified protease. Its yield of activity was 62% and chlorine content was 175 ppm. It did not present a skin sensitization and mean score was zero. In the shelf life test of the obtained product at 40° C. for 6 months, the solubility in the phosphate buffer (pH 6.8) was good and activity deterioration was not seen. Furthermore, after the test, residual activity in thermal stability assessment in the presence of water (60° C. ×6 hours) was 99%. No change was observed.

EXAMPLES 15 to 18

The same dextran 125 g as in Example 1 was dissolved in 2.5 l of water. Cyanuric trichloride in 600 ml of acetone was therewith in conditions shown in Table 5 mentioned below. Adjustment of pH was done using 1N-NaOH and the temperature range was 18° C. to 22° C. After dropping, 0.1N-HCl was added thereto to adjust to pH 3, then the resulting was added to 20 l of acetone to filtrate the deposited crystal and to clean with acetone to give an active dextran.

Then, 10 g of said active dextran was dissolved in 100 ml of water and the same protease as in the Example 1 which was dissolved in 10 ml of water was added thereto and further 100 ml of 0.2M borate buffer (pH 9.2) was added. The mixture was reacted at 25° C. for 20 hours. Here the protease with 0.06 mmol/g of reactive amino groups was used to arrange so that molar ratio of the reactive chlorine content in the active dextran to the reactive amino groups of the protease was 10.

After above reaction of modification, 1.3 g of glycine was added and dissolved in the reaction and then heat treated at 60° C. for 30 hours, subsequently each was cleaned four times by ultrafiltration to remove low molecular substance, concentrated and lyophilized to give light brown powder.

Such modified protease powder was assessed according to aforementioned methods in activity, protein surface amino groups modification rate, skin sensitization and stability in aqueous medium. The results are shown in Table 5.

For a test of said stability in aqueous medium, a test modified protease was dissolved in 50 mmol/g phosphate buffer (pH 6.8) to a concentration of 0.5 mg protein/ml. This test solution was incubated at 60° C. for 6 hours or at 40° C. for 3 months.

TABLE 5

| | Cyanuric trichloride (g) | pH | Dropping time of cyanuric trichloride solution (min.) | Reactive chlorine content in active polysaccharide (mmol/g) | Modification rate for surface amino groups (%) | Skin sensitization potential | Yield of activity (%) | Residual activity in aqueous medium (%) 60° C., 6 hrs. | Residual activity in aqueous medium (%) 40° C., 3 months |
|---|---|---|---|---|---|---|---|---|---|
| Examples 15 | 18.5 | 9.5~11 | 25 | 0.23 | 28 | 0.6 | 75 | 71 | 60 |
| 16 | 18.5 | 8.5~9.5 | 30 | 0.47 | 75 | 0.2 | 64 | 97 | 95 |
| 17 | 25.0 | 8~9 | 15 | 0.75 | 81 | 0 | 59 | 99 | 100 |
| 18 | 37.5 | 8.5~10 | 15 | 0.93 | 85 | 0 | 55 | 99 | 100 |

*In the above Example 15, a mixed solvent of water-acetone (1:2 v/v) was used as a solvent of the cyanuric trichloride.

From the above results, when the reactive chlorine content in the active dextran is 0.4 to 1.2 mmol/g, modified protease excellent in stability in aqueous medium and skin sensitization can be prepared.

EXAMPLES 19 to 22

10 g of active dextran which was prepared as well as in the Example 16 was dissolved in 100 ml water and protease was added thereto as well as in Examples 15 to 18 to be reacted. The protease with 0.72 mmol of reactive amino groups amount was used and ratio of the reactive chlorine content to reactive amino groups amount was set forth as shown in Table 6.

Assessment results of characteristics of the various modified protease thus obtained are also shown in Table 6.

TABLE 6

| | Reactive chlorine content/ Reactive amino groups | Modification rate for surface amino groups (%) | Skin sensitization potential | Yield of activity (%) | Residual activity in aqueous medium (%) 60° C., 6 hours | Residual activity in aqueous medium (%) 40° C., 3 months |
|---|---|---|---|---|---|---|
| Examples 19 | 1.5 | 25 | 0.6 | 75 | 72 | 63 |
| 20 | 2 | 59 | 0.1 | 67 | 91 | 85 |
| 21 | 6 | 79 | 0 | 58 | 99 | 100 |
| 22 | 9 | 81 | 0 | 53 | 99 | 100 |

From the above results, in the case of not less than two at molar ratio of reactive chloride content to reactive amino groups amount, modified protease excellent in both stability and safety can be obtained. When the value is not less than five, further preferable results can be obtained.

EXAMPLES 23 to 26

Modified protease was prepared as well as in said Examples 15 to 18. But the amount of cyanuric trichloride used in preparation of active dextran, reactive pH, reaction time were applied as shown in Table 7. Protease with reactive amino groups amount 0.55 mmol/g was used. In the modification reaction, 8 time amount of active dextran to protease in weight ratio was provided.

Assessment results of thus obtained modified protease are shown in Table 7.

TABLE 7

| | Cyanuric trichloride (g) | pH | Dropping time of cyanuric trichloride solution (min.) | Reactive chlorine content in active polysaccharide (mmol/g) | Modification rate for surface amino groups (%) | Skin sensitization potential | Yield of activity (%) | Residual activity in aqueous medium (%) 40° C., 3 months |
|---|---|---|---|---|---|---|---|---|
| Examples 23 | 25 | 7~7.5 | 15 | 0.25 | 24 | 0.5 | 79 | 62 |
| 24 | 25 | 7.5~8.5 | 15 | 0.67 | 82 | 0 | 58 | 100 |
| 25 | 25 | 8.5~9.5 | 15 | 0.72 | 82 | 0 | 53 | 100 |
| 26 | 25 | 9.5~11 | 15 | 0.41 | 71 | 0.2 | 67 | 85 |

It is apparent from the above results that by arranging synthetic reaction condition of active dextran appropriately, modified protease with superior stability and safety can be obtained.

Only 0.2% of the modified protease obtained in said Example 25 was mixed with various basic mixture shown in Table 8 and treated thermally at 60° C. for six hours. The treated modified protease was determined the activity, and assessed the stability compared with unmodified protease. The results are shown in Table 8.

TABLE 8

| | | Residual activity (%) | |
|---|---|---|---|
| | | Examples | unmodified |
| Tween 20 *1 | 0.1% | 100 | 6 |
| Hyaluronic acid | 0.1% | | |
| 0.1 M-Phosphate buffer (pH 7) | 10.0% | | |
| Ethanol | 5% | 100 | 5 |
| 0.1 M-Phosphate buffer (pH 7) | 10.0% | | |
| Glycerol | 10.0% | 98 | 19 |
| 0.1 M-Phosphate buffer (pH 7) | 10.0% | | |

*1: Tween 20 (Manufactured by Wako Pure Chemical)

It is apparent from the above results that in various model product form, modified protease of Examples according to the present invention presents excellent stability.

Examples of cosmetic composition to which the modified protease according to the present invention is applied are described below.

EXAMPLE 27

Skin lotion of below-mentioned formula was prepared in ordinary method.

| Formula of skin lotion | Weight part |
|---|---|
| Modified protease in Example 17 | 0.2 |
| Sodium hyaluronic acid | 0.1 |
| Polyoxyethylene sorbitan mono-laurate (20E.O.) | 0.1 |
| Perfume | 0.01 |
| Blue-1 | small amount |
| Purified water | rest |

EXAMPLE 28

The procedure of Example 27 was repeated except that modified protease of Example 22 was used in lieu of that of Example 17 to prepare skin lotion.

EXAMPLE 29

The procedure of example 27 was repeated except that modified protease of Example 1 was used in lieu of that of Example 17 to prepare skin lotion.

EXAMPLE 30

The procedure of Example 27 was repeated except that protease of Example 2 was used in lieu of that of Example 17 to prepare skin lotion.

COMPARATIVE EXAMPLE 5

The procedure of Example 27 was repeated except that unmodified protease was used in lieu of modified protease of Example 17 to prepare skin lotion.

COMPARATIVE EXAMPLE 6

The procedure of Example 27 was repeated except that immobilized protease which was prepared as below-mentioned was used in lieu of modified protease of Example 17 to prepare skin lotion.

Preparation of Immobilized Protease

In 20 parts of water was dissolved 20 parts of calcium chloride. With the solution was mixed 80 parts of methanol. Then 5 parts of nylon powder (average particle diameter: 6 to 10 μm) were added thereto. The mixture was dispersed and stirred at 50° C. for 30 minutes. After it is collected and washed with water, it is dipped in 100 parts of 3.5M-HCl and stirred at 45° C. for 50 minutes. After washing it with water, it is dipped in 50 parts of 0.1M-sodium borate buffer (pH 8.5) containing 10% of glutaraldehyde and subsequently it was washed with the same buffer. The treated powder was added to 50 parts of 0.05M-sodium phosphate buffer (pH 7.5) containing 1 part of the same protease as that of Example 1. The mixture was reacted at 10° C. for 5 hours, then washed with water to obtain carrier-bound type immobilized protease powder.

Thermal stability, antigenicity, skin sensitivity, practical characteristics and preservation stability are measured and assessed on obtained products in said Examples 27 to 30 and Comparative Examples 5 to 6. These results are shown in Table 9. But among said properties, thermal stability, antigenicity and skin sensitization were determined according to aforementioned method and others were according to below-mentioned method.

Practical Characteristics

The practical test was conducted once a day by 20 special examiners continuously for three days. Questionnaire of below-mentioned testing items were replied by them.
 (1) Simplicity in use:
   Number who replied that the use was simple.
 (2) Roughness in use:
   Number who replied that roughness was felt in use.
 (3) Irritating feeling after use:
   Number who replied that irritation was felt on skin or head skin after use.
 (4) Smoothness after use:

Number who replied that skin or hair became smoothly after use.

(5) Gloss after use:
Number who replied that glossy skin or hair was given after use.

Preservation Stability

Samples were sealed, placed in a constant temperature bath at 40° C. and left as they were for three months in a state of cutting light, and then changes in color and smell were observed.

TABLE 9

|  |  | Examples | | | | Comparative Examples | |
|---|---|---|---|---|---|---|---|
|  |  | 27 | 28 | 29 | 30 | 5 | 6 |
| Thermal stability (%) | | 93 | 87 | 80 | 85 | 10 | 65 |
| Antigenicity | | ○ | ○ | ○ | ○ | X | Δ |
| Skin sensitization potential | | 0 | 0 | 0 | 0 | 5.0 | 1.0 |
| Practical characteristics | Simplicity in use | 20 | 20 | 20 | 20 | 20 | 12 |
| | Roughness in use | 0 | 0 | 0 | 0 | 0 | 20 |
| | Irritating feeling after use | 0 | 0 | 0 | 0 | 17 | 3 |
| | Smoothness after use | 20 | 20 | 20 | 20 | 2 | 9 |
| | Gloss after use | 20 | 20 | 20 | 20 | 0 | 6 |
| Preservation stability | Change in color | nil | nil | nil | nil | Slightly yellow | nil |
| | Change in smell | nil | nil | nil | nil | Slightly yellow | nil |

It is apparent from the above results that products of Examples are all superior to those of Comparative Examples in various characteristic performance.

EXAMPLE 31

Skin cream with below-mentioned formula was prepared as follows.

| Formula of Skin cream | Weight part |
|---|---|
| Modified protease of Example 17 | 1.5 |
| Oil phase | |
| Liquid paraffin | 35.0 |
| Cetyl alcohol | 5.0 |
| Polyoxyethylene sorbitan mono-oleate (20E.O.) | 7.0 |
| Water phase | |
| Maltitol | 10.0 |
| Purified water | 41.4 |
| Methylparabene (Methyl-p-oxybenzoate) | 0.1 |

Said oil phase gredients were uniformly dissolved by heating at 80° C. and to the dissolved oil phase gredients were added said water phase gredients which were also uniformly dissolved by heating at 80° C. The mixture was cooled stirring to 40° C. to add modified protease. The modified protease added mixture was cooled to 30° C. to give required skin cream.

EXAMPLE 32

Hair cream with below-mentioned formula was prepared as follows.

| Formula of hair cream | Weight part |
|---|---|
| Modified protease of Example 22 | 0.5 |
| Oil phase | |
| Octyldodecyl myristate | 35.0 |
| Cetyl alcohol | 5.0 |
| Sorbitan sesquistearate | 3.0 |

| Formula of hair cream | Weight part |
|---|---|
| Water phase | |
| Glycerol | 15.0 |
| Polyoxyethylene sorbitan mono-oleate (20E.O.) | 5.0 |
| Methylparabene (Methyl-p-oxybenzoate) | 0.1 |
| Purified water | 34.4 |

Said oil phase gredients are uniformly dissolved by heating at 80° C. To the dissolved oil phase gredients were added said water phase gredients which were also uniformly dissolved by heating at 80° C. The mixture was cooled stirring to 40° C. to add modified protease. The modified protease added mixture was cooled to 30° C. to give required hair cream.

EXAMPLE 33

Cleansing milk with below-mentioned formula was prepared as follows.

| Formula of Cleansing milk | Weight part |
|---|---|
| Modified protease of Example 1 | 0.3 |
| Oil phase | |
| Liquid paraffin | 50.0 |
| Glycerol mono-stearate | 5.0 |
| Cetyl alcohol | 3.0 |
| Sorbitan sesquistearate | 5.0 |
| Water phase | |
| Sodium cetyl sulphate | 1.0 |
| Sorbytol | 10.0 |
| Purified water | 25.7 |

Said oil phase gredients were uniformly dissolved by heating at 80° C. To the dissolved oil phase gredients were added said water phase gredients which were also uniformly dissolved by heating at 80° C. The mixture was cooled stirring to 40° C. to add modified protease. The modified protease added mixture was cooled to 30° C. to give required cleansing milk.

EXAMPLE 34

Cream soap with below-mentioned formula was prepared as follows.

| Formula of Cream soap | Weight part |
|---|---|
| Modified protease of Example 2 | 1.0 |
| Water phase | |
| Sodium myristate | 30.0 |
| Sodium laurate | 20.0 |
| Glycerol | 35.0 |
| Purified water | 14.0 |

Said water phase gredients were uniformly dissolved by heating at 80° C. for one hour, and the dissolved water phase gredients were cooled stirring them. The modified protease was added thereto at 40° C. and the mixture was cooled to 30° C. to give required cream soap.

EXAMPLE 35

Required powder foundation was given by stirring and mixing materials of below-mentioned formula uniformly.

| Formula of Powder foundation | Weight part |
| --- | --- |
| Talc | 10 |
| Sericite | 30 |
| Titanium oxide | 9 |
| Mica | 30 |
| Color pigment | 20 |
| Modified protease of Example 10 | 1 |

Characteristic performance and shelf life were determined and assessed as well aforementioned method. These results are shown in below-mentioned Table 10.

TABLE 10

|  |  | Examples | | | | |
| --- | --- | --- | --- | --- | --- | --- |
|  |  | 31 | 32 | 33 | 34 | 35 |
| Practical character-istics | Simplicity in use | 20 | 20 | 20 | 20 | 20 |
|  | Roughness in use | 0 | 0 | 0 | 0 | 0 |
|  | Irritating feeling after use | 0 | 0 | 0 | 0 | 0 |
|  | Smoothness after use | 20 | 20 | 19 | 20 | 20 |
|  | Gloss after use | 20 | 20 | 20 | 20 | 20 |
| Preservation stability | Change in color | nil | nil | nil | nil | nil |
|  | Change in smell | nil | nil | nil | nil | nil |

It is apparent from the above results that the modified proteases according to Examples are invariably satisfactory in performance characteristic and shelf life.

Effects of Invention

Thus, being such that a protease is coupled to a polysaccharide via a triazine ring, the modified protease of the present invention has been substantially or completely suppressed in antigenicity and skin sensitization potential and been remarkably improved in thermal stability. Moreover, with a reduced loss of activity due to modification, the modified protease exhibits exceptionally high activity. Because its stability is not affected even in the presence of high concentrations of surfactants, the modified protease of the invention finds application in various uses.

The cosmetic composition according to the invention, containing the above stable and safe modified protease, is easy to use and does not irritate the skin or elicit allergic responses. It does not undergo change in odor or color on storage. Moreover, when applied to the skin, the modified protease removes the aged horny layer to smoothen the skin, thus producing a marked cosmetic effect.

I claim:

1. A method of producing a modified protease, comprising the steps of (a) reacting a polysaccharide with cyanuric trichloride to synthesize a triazine ring-bound polysaccharide, (b) then reacting this triazine ring-bound polysaccharide with a protease, the reactive chlorine content of said triazine ring-bound polysaccharide being controlled within the range of 0.4 to 1.2 mmol/g, and the molar ratio of the reactive chlorine of said triazine ring-bound polysaccharide to the reactive amino groups of said protease being insured to be not less than 2:1, and (c) heat-treating the reaction product in an aqueous solution of an amino group-containing low molecular compound to adjust the content of atomic halogen attached to the triazine ring to less than 500 ppm.

2. A method of producing a modified protease according to claim 1, wherein the step of reacting the polysaccharide with cyanuric trichloride, the cyanuric trichloride used is dissolved in a non-aqueous polar solvent inert to cyanuric trichloride, the polysaccharide is dissolved in water, and the polysaccharide and cyanuric trichloride are reacted in a ratio of 1:0.5 through 1:0.1 by weight.

3. A method of producing a modified protease according to claim 2, wherein the solvent in which cyanuric trichloride is dissolved is acetone.

4. A method of producing a modified protease according to claim 1, wherein the reaction of the polysaccharide with cyanuric trichloride is carried out at pH 7.75 to 9.5.

* * * * *

UNITED STATES PATENT AND TRADEMARK OFFICE
CERTIFICATE OF CORRECTION

PATENT NO. : 5,133,968

DATED : July 28, 1992

INVENTOR(S) : Hiroshi NAKAYAMA et al.

It is certified that error appears in the above-identified patent and that said Letters Patent is hereby corrected as shown below:

In Column 7, line 51, insert paragraph heading --Assessment of antigenicity--.

Signed and Sealed this

Ninth Day of November, 1993

Attest:

BRUCE LEHMAN

Attesting Officer    Commissioner of Patents and Trademarks